US006892739B2

(12) United States Patent
Merz et al.

(10) Patent No.: US 6,892,739 B2
(45) Date of Patent: May 17, 2005

(54) MICROBICIDALLY ACTIVE TENSIDES

(75) Inventors: Thomas Merz, Hilden (DE); Bernhard Meyer, Mettmann (DE); Khalil Shamayeli, Dusseldorf (DE)

(73) Assignee: Ecolab GmbH & Co. oHG, Dusseldorf (DE)

( * ) Notice: Subject to any disclaimer, the term of this patent is extended or adjusted under 35 U.S.C. 154(b) by 0 days.

(21) Appl. No.: 10/258,161

(22) PCT Filed: Apr. 11, 2001

(86) PCT No.: PCT/EP01/04152

§ 371 (c)(1),
(2), (4) Date: May 6, 2003

(87) PCT Pub. No.: WO01/80907

PCT Pub. Date: Nov. 1, 2001

(65) Prior Publication Data

US 2003/0181348 A1 Sep. 25, 2003

(30) Foreign Application Priority Data

Apr. 20, 2000 (DE) .......................... 100 20 145

(51) Int. Cl.⁷ .............................. B08B 3/00; C11D 1/72; C11D 3/37; A61L 2/18
(52) U.S. Cl. ..................... 134/25.2; 134/25.3; 134/38; 134/39; 134/40; 134/41; 134/42; 8/137; 510/360; 510/421; 510/475; 510/535; 422/28; 422/5
(58) Field of Search ................... 510/360, 421, 510/475, 535; 134/25.2, 25.3, 38–42; 8/137; 422/5, 28

(56) References Cited

U.S. PATENT DOCUMENTS

| 4,780,237 A | * | 10/1988 | Schmid et al. .......... 252/174.22 |
| 5,364,552 A | * | 11/1994 | Merz et al. ............ 252/174.22 |
| 5,798,329 A | | 8/1998 | Taylor et al. |
| 5,912,221 A | * | 6/1999 | Van Leeuwen et al. ..... 510/360 |
| 6,248,708 B1 | * | 6/2001 | Merz et al. ................. 210/404 |
| 2003/0181348 A1 | * | 9/2003 | Merz et al. ................. 510/421 |

FOREIGN PATENT DOCUMENTS

| DE | 31 11 158 | 9/1982 |
| DE | 40 07 758 | 9/1991 |
| DE | 40 29 777 | 3/1992 |
| EP | 0 156 275 | 10/1985 |
| EP | 0 342 499 | 11/1989 |
| EP | 0 343 605 | 11/1989 |
| EP | 0 551 975 | 7/1993 |
| EP | 0 592 876 | 4/1994 |
| EP | 0 612 170 | 8/1994 |
| EP | 0 620 013 | 10/1994 |
| EP | 0 709 089 | 5/1996 |
| GB | 2 338 242 | 12/1999 |
| WO | WO 98/10049 | * 3/1998 ........... C11D/1/825 |

* cited by examiner

Primary Examiner—Brian P. Mruk
(74) Attorney, Agent, or Firm—Merchant & Gould P.C.

(57) ABSTRACT

The invention relates to the use of tenside agents containing selected non-ionic tensides, for use in cleaning and/or disinfecting processes and/or cleaning and/or disinfecting preparations.

20 Claims, No Drawings

MICROBICIDALLY ACTIVE TENSIDES

This invention relates to the use of a surface-active composition as a disinfecting component in cleaning and/or disinfecting processes and/or preparations.

European patent application EP-A-0 342 499 describes a cleaning and disinfecting process in which the surfaces to be disinfected are contacted with a cleaning/disinfecting solution which contains at least one low-foaming nonionic surfactant, at least one proteolytic enzyme, at least one complexing agent and at least one aldehyde from the group consisting of formaldehyde and aliphatic dialdehydes containing 2 to 8 carbon atoms and which has a pH value of 6 to 8, the solution being heated to 55 to 65° C., kept at that temperature for 1 to 15 minutes and then removed. The surfaces to be treated are then rinsed twice with water, the water being heated to 55 to 65° C. in the second rinse at least, and thereafter are dried with sterilized air heated to 40 to 60° C.

It is known from European patent application EP-A-0 156 275 that amine compounds obtained by reacting compounds corresponding to the formula $R^1NHCH_2CH_2CH_2NH_2$, where $R^1$ is a linear alkyl group containing 12 to 14 carbon atoms, with compounds corresponding to the formula $R^2OCOCH_2CH_2CHNH_2COOH$, where $R^2$ is an alkyl group containing 1 to 4 carbon atoms or a hydrogen atom, in a molar ratio of 1:1 to 1:2 at 60 to 175° C. can be used as antimicrobial agents. These reaction products are now also known by the name of glucoprotamine.

German patent application DE-A-40 07 758 describes a water-based surfactant-containing cleaner/disinfectant concentrate which contains as antimicrobial agents the amine compounds described in European patent application EP-A-0 156 275 in combination with selected quaternary ammonium compounds. DE-A-40 07 758 also describes a process for the spray cleaning and disinfection of objects in automatic machines which comprises the steps of a) spraying on an aqueous disinfecting cleaning solution prepared by diluting the described cleaning concentrate at elevated temperature, optionally b) spraying on an aqueous, optionally surfactant-containing rinse agent solution and optionally c) drying, preferably with hot air.

EP-A-343 605 describes a liquid aldehyde-free disinfectant which contains N,N-bis-(3-aminopropyl)-laurylamine as its active component.

European patent application EP-A-0 620 013 describes a disinfectant for communal toilet systems and similar installations which is used manually. It contains salts of amines with the formula $RN[(CH_2)_n—NH_2][(CH_2)_m—NH_2]$ or $RNH[(CH_2)_p—NH_2]$, where R is a linear or branched alkyl or alkenyl group containing 6 to 22 carbon atoms, n and m assume values of 4 to 12 and p has a value of 2 to 12. Because of their corrosive effect on metals, such as steel, and plastics, the preparations are used at low temperatures of up to 50°.

European patent application EP-A-0 551 975 describes a disinfectant concentrate and an amine- and alcohol-based disinfectant and their use, the alcohol component containing at least one aromatic alcohol and the amine component containing at least one secondary and/or tertiary alkylamine with no hydroxy groups. The ready-to-use solution has a pH of 7 to 12. The disinfectant is used in particular as a bactericide, more especially as a mycobactericide, fungicide or virucide. European patent application EP-A-0 612 170 also relates to an amine- and alcohol-containing disinfectant in which the alcohol component comprises at least one incompletely water-miscible glycol ether and the amine component comprises at least one secondary and/or tertiary alkylamine with no hydroxy groups.

DE 31 11 158 discloses disinfecting cleaning boosters which contain a nonionic surfactant, a disinfecting quaternary ammonium compound, water and a diammonium salt of certain dicarboxylic acids.

GB 2,338,242 describes aqueous germicidal surfactant mixtures containing anionic surfactants, a cationic germicidal surfactant, a nonionic surfactant and an optical brightener.

The disinfectants and cleaners and disinfecting/cleaning processes described in the documents cited above have a common disadvantage: to achieve the required disinfecting performance, specially prepared disinfectants have to be added. Aldehydes, quaternary ammonium compounds, oxidizing components based on peroxide- or halogen-containing compounds, organic halogen compounds, phenol derivatives are mentioned as examples. It is known that the use of disinfectants in practice can lead to problems. For example, disinfectants can cause allergic reactions in people coming into contact with them in whatever form. In addition, where such compounds as aldehydes or amines are used, coatings can be formed on the surfaces to be disinfected by reaction with cleaning residues. In many cases, the ecological profile of disinfectants is also negative. This can apply both to their toxicity towards aquatic organisms and to their degradability. In most cases and especially in cleaning and disinfecting processes where surface-active cleaning components are used, disinfectants also make little or no contribution to the cleaning result and only incur additional raw material costs. The use of oxidative disinfectants can have unpleasant consequences, such as an irritating effect on the skin or fire-promoting properties. In addition, storage, handling and transportation problems are known to arise where oxidative disinfectants are used. Where oxidative disinfectants are used together with colored textiles, the dyes can be bleached out. In addition, it is known that textiles or textile fibers can be permanently damaged where per acids, hydrogen peroxide and other peroxides are used.

Accordingly, the problem addressed by the present invention was to provide surface-active components of which the use would eliminate the need for additional disinfectants and which would still deliver satisfactory bleaching performance.

The problem stated above has surprisingly been solved by the use of selected nonionic surfactants. Accordingly, the present invention relates to the use of a surface-active composition containing—based on the composition as a whole a) 5 to 100% by weight, preferably 5 to 60% by weight and more particularly 5 to 40% by weight of one or more nonionic surfactants corresponding to general formula (I):

$$R^1—(OC_2H_4)_n—(OC_3H_6)_m—OH \qquad (I)$$

in which $R^1$ is a linear or branched alkyl or alkenyl group containing 8, 10, 12 or 14 carbon atoms, preferably 10, 12 or 14 carbon atoms and more particularly 12 to 14 carbon atoms and the sum of the average degree of ethoxylation n and the average degree of propoxylation m is between 0.5 and 7, preferably between 1 and 5 and more particularly between 1 and 3, m even being 0, and/or b) 5 to 100% by weight, preferably 5 to 60% by weight and more particularly 5 to 40% by weight of one or more nonionic surfactants corresponding to general formula (II):

in which $R^2$ is a linear or branched alkyl or alkenyl group containing 7, 9, 11, 13 or 15 carbon atoms, preferably 9, 11 or 13 carbon atoms and more particularly 11 or 13 carbon atoms and the sum of the average degree of ethoxylation r and the average degree of propoxylation s is between 0.5 and 7, preferably between 1 and 5 and more particularly between 1 and 3, s even being 0, and c) optionally water and/or other auxiliaries and/or active substances, the sum total of all the constituents not exceeding 100% by weight, the ratio by weight of a) to b) in the mixture preferably being between 4:1 and 1:4, as a disinfecting component in cleaning and/or disinfecting processes and/or preparations.

It is not disclosed anywhere in the prior art that excellent disinfecting results can be obtained by the use of the described surfactants in accordance with the invention.

The use according to the invention is preferably carried out by separate addition of the compositions to be used in accordance with the invention in the cleaning and/or disinfecting process, as a disinfection booster so to speak, or by addition of compositions to be used in accordance with the invention to the preparation of the cleaner and/or disinfectant.

In a preferred embodiment, the disinfecting result is achieved without the addition of other disinfecting components.

In another preferred embodiment, the surface-active composition to be used in accordance with the invention additionally contains—based on the composition as a whole—up to 40% by weight, preferably 0.5 to 35% by weight and more particularly 0.5 to 8% by weight of an anionic surfactant solid at room temperature, more particularly alkyl benzenesulfonic acid, alkali metal alkyl benzenesulfonate and/or alkali metal alkyl or alkenyl sulfate.

Suitable synthetic anionic surfactants, which may be incorporated in solid, fine-particle and substantially water-free form in the surfactant mixture according to the invention, include in particular those of the sulfonate or sulfate type which are normally present as alkali metal salts and preferably as sodium salts. However, the above-mentioned surfactants of the sulfonate type may also be used in the form of their free acids. Suitable anionic surfactants of the sulfonate type are alkyl benzenesulfonates with linear $C_{9-13}$ alkyl chains, more particularly dodecyl benzenesulfonate, linear alkanesulfonates containing 11 to 15 carbon atoms which may be obtained by sulfochlorination or sulfoxidation of alkanes and subsequent saponification or neutralization, salts of sulfofatty acids and esters thereof which are derived from saturated $C_{12-18}$ fatty acids sulfonated in particular in the α-position and lower alcohols, such as methanol, ethanol and propanol, and olefin sulfonates obtained for example by $SO_3$ sulfonation of terminal $C_{12-18}$ olefins and subsequent alkaline hydrolysis. Suitable surfactants of the sulfate type are, in particular, primary alkyl sulfates with preferably linear $C_{10-20}$ alkyl chains which contain an alkali metal, ammonium or alkyl- or hydroxyalkyl-substituted ammonium ion as counter-cation. Derivatives of linear alcohols containing in particular 12 to 18 carbon atoms and branched-chain analogs thereof, so-called oxoalcohols, are particularly suitable. Accordingly, the sulfation products of primary fatty alcohols with linear dodecyl, tetradecyl, hexadecyl or octadecyl groups and mixtures thereof are particularly useful. Particularly preferred alkyl sulfates contain a tallow alkyl group, i.e. mixtures essentially containing hexadecyl and octadecyl groups. The alkyl sulfates may be obtained in known manner by reacting the corresponding alcohol component with a typical sulfating agent, more particularly sulfur trioxide or chlorosulfonic acid, and subsequent neutralization with alkali metal, ammonium or alkyl- or hydroxyalkyl-substituted ammonium bases. In addition, the sulfated alkoxylation products of the alcohols mentioned, so-called ether sulfates, may be present in the compositions. These ether sulfates preferably contain 2 to 30 and more particularly 4 to 10 ethylene glycol groups per molecule.

Preferred synthetic anionic surfactants are alkyl benzenesulfonates and/or alkyl sulfates.

In one preferred embodiment, the surface-active composition to be used in accordance with the invention contains additional components with complexing properties and/or solubilizers and/or surface-active components.

The components with complexing properties are preferably selected from nitrilotriacetic acid, ethylenediamine tetraacetic acid, methyl glycine diacetic acid, gluconic acid, citric acid, dicarboxymethyl-L-glutamic acid, serine diacetic acid, imidosuccinic acid and from the group of polycarboxylic acids and phosphonic acids and salts thereof.

Suitable polycarboxylic acids are, for example, polyacrylic acids and copolymers of maleic anhydride and acrylic acid and the sodium salts of these polymer acids. Commercially available products are, for example, Sokalan® CP 5 and PA 30 (BASF), Alcosperse® 175 and 177 (Alco), LMW® 45 N and SPO2 ND (Norsohaas). Suitable native polymers include, for example, oxidized starch (for example DE 42 28 786) and polyamino acids, such as polyglutamic acid or polyaspartic acid, for example from such manufacturers as Cygnus, Bayer, Rohm & Haas, Rhône-Poulenc or SRCHEM.

Suitable phosphonic acids are, for example, 1-hydroxyethane-1,1-diphosphonic acid, diethylenetriamine pentamethylene phosphonic acid or ethylenediamine tetramethylene phosphonic acid and alkali metal salts thereof.

In a particularly preferred embodiment, the components with complexing properties are selected from nitrilotriacetic acid, polyaspartic acid or polycarboxylic acids, which preferably go back to polymerization of aspartic acid with other carboxylic acids, and gluconic acid.

In addition, solubilizing agents are preferably selected from the group of anionic surfactants, more particularly from the sulfonates/sulfonic acids and above all from cumene, xylene, octyl, naphthyl and alkyl benzenesulfonates/sulfonic acids (the alkyl group containing between 6 and 16 carbon atoms) or mixtures of these compounds and/or other compounds which act as solubilizers.

Other preferred surface-active components are amine oxide derivatives. In a particularly preferred embodiment, the amine oxide derivative is a trialkylamine oxide with one $C_{8-20}$ alkyl group and two alkyl groups with a smaller number of carbon atoms in the alkyl chain, the two shorter alkyl groups being the same or different. In a most particularly preferred embodiment, the amine oxide derivative is tallow fatty bis-(2-hydroxyethyl)-amine oxide, oleyl-bis-(2-hydroxyethyl)-amine oxide, coconut bis-(2-hydroxyethyl)-amine oxide, tetradecyl dimethyl amine oxide and/or alkyl dimethyl amine oxide with 12 to 18 carbon atoms in the alkyl chain.

Additional preferred surface-active components are selected from the groups of anionic, cationic, nonionic, amphoteric surfactants, protein hydrolyzates, silicone compounds and phosphoric acid esters and salts thereof.

The surface-active compositions to be used in accordance with the invention may contain alkyl polyglucosides as additional nonionic surfactants. Alkyl polyglucosides are normally obtained on an industrial scale by condensation of fatty alcohols with glucose or polyglucose and are commercially available in various forms. Examples of alkyl polyglucosides which are particularly suitable for the use according to the invention are the products Glucopon® 600 (Henkel) and Triton® BG10 (Rohm & Haas).

In addition to the compounds corresponding to formula I and II, nonionic surfactants suitable for use in the surface-active compositions to be used in accordance with the invention are other alkoxylated alkyl alcohols containing 8 to 22 carbon atoms in the alkyl chain. In a particularly preferred embodiment, the compositions contain at least one compound from the groups of mixed ethoxylates/propoxylates of branched or unbranched alkyl alcohols containing 8 to 22 carbon atoms in the alkyl chain and end-capped ethoxylates of branched or unbranched alkyl alcohols containing 8 to 22 carbon atoms in the alkyl chain. In a most particularly preferred embodiment, the compositions contain at least one compound from the groups of ethoxylated and propoxylated alkyl alcohols containing 12 to 22 carbon atoms in the alkyl moiety, butyl ethers of ethoxylated alkyl alcohols containing 12 to 22 carbon atoms in the alkyl moiety and methyl ethers of ethoxylated alkyl alcohols containing 12 to 22 carbon atoms in the alkyl moiety. In one special case, the compositions contain butyl ethers and methyl ethers of ethoxylated 2-octyl-1-dodecanol. Nonionic surfactants particularly suitable for the production of formulations for the use according to the invention are, for example, Plurafac® LF 403 and Plurafac® 431 (BASF) and Dehypon® LT 104 and Dehypon® G 2084 (Henkel).

In a preferred embodiment, the surface-active compositions to be used in accordance with the invention contain as phosphoric acid esters phosphoric acid ester compounds which preferably include at least one salt of a phosphoric acid partial ester and, more particularly, at least one alkali metal salt of a phosphoric acid partial ester of alkoxylated alkyl phenol.

The phosphoric acid esters are surface-active substances which are preferably derived from long-chain aliphatic or araliphatic alcohols. Salts of phosphoric acid partial esters, especially those of alkoxylated alkylphenols, have proved to be particularly suitable. Preferred alkali metal salts are the sodium and potassium salts, the potassium salts being particularly preferred. Surface-active phosphoric acid partial esters preferably used in accordance with the invention are commercially obtainable. One example of an active substance of this type which is particularly suitable for use in accordance with the invention is the product Triton® H 66 (Rohm & Haas).

Although the use of the surface-active compositions to be used in accordance with the invention leads to satisfactory disinfecting results in most cases, it can be advisable from case to case to add additional antimicrobial components. In this case, the additional antimicrobial components are preferably selected from alcohols, aldehydes, antimicrobial acids, carboxylic acid esters, acid amides, phenols, phenol derivatives, diphenyls, diphenylalkanes, urea derivatives, oxygen and nitrogen acetals and formals, benzamidines, isothiazolines, phthalimide derivatives, pyridine derivatives, antimicrobial surfactants, guanidines, antimicrobial amphoteric compounds, quinolines, 1,2-dibromo-2,4-dicyanobutane, iodo-2-propynyl butyl carbamate, iodine, iodophores, peroxides. In a particularly preferred embodiment, the additional antimicrobial components are selected from ethanol, n-propanol, i-propanol, 1,3-butanediol, phenoxyethanol, 1,2-propylene glycol, glycerol, undecylenic acid, citric acid, 2-benzyl-4-chlorophenol, 2,2'-methylene-bis-(6-bromo-4-chlorophenol), 2,4,4'-trichloro-2'-hydroxydiphenylether, N-(4-chlorophenyl)-N-(3,4-dichlorophenyl)-urea, N,N'-(1,10-decanediyldi-1-pyridinyl-4-ylidene)-bis-(1-octaneamine)-dihydro-chloride, N, N'-bis-(4-chlorophenyl)-3,12-diimino-2,4,11,13-tetraaza-tetradecane diimidoamide, quaternary ammonium compounds, guanidines, amphoterics and gluconic acid, citric acid, lactic acid, malic acid, tartaric acid, salicylic acid, p-hydroxybenzoic acid.

Preferred application forms of the surface-active compositions to be used in accordance with the invention are aqueous solutions, gels, emulsions, pastes, dispersions, solid shaped bodies and powders.

In another preferred embodiment, the surface-active compositions to be used in accordance with the invention are contacted with the surfaces to be cleaned and/or disinfected in concentrated or dilute form either by immersion or by filling the article to be disinfected and/or by application aids. Preferred application aids are sponges, cloths, rags, brushes, mops, rubber blade coaters, sprays and foam aerosols.

In a preferred embodiment, the surfaces to be treated are simultaneously cleaned and disinfected by using the surface-active compositions to be used in accordance with the invention.

In a preferred use, textiles are contacted with a surface-active composition to be used in accordance with the invention in concentrated or dilute form at low temperatures of 10 to 70° C. and are washed and disinfected in the process. It has been found that it is possible under these conditions to obtain satisfactory disinfection even without the addition of oxidizing disinfectants, such as peracetic acid for example.

This is also of considerable importance because, where per acids, for example peracetic acid, are used, textiles or textile fibers are permanently damaged in the washing process. This applies particularly to the washing of delicate textiles consisting of materials such as wool, silk, polyacrylics, viscose, polyamide, acetate and lyocell.

The extent of the damage is additionally influenced by the conditions of the washing process, such as mechanics, temperature, time, concentration and type of chemistry.

Textiles are damaged more or less seriously, depending on the conditions. In the case of woolen textiles, vigorous mechanical action causes the textile fibers to become irreversibly entangled, so that wool shrinks to a considerable extent. The washing conditions also determine whether and to what extent the polymer structure of the textiles is affected. Any change in the polymer structure reduces the tensile strength of textiles. In the case of wool, this results in increased alkali solubility and, in the case of cotton, in a serious loss of tensile strength, i.e. in a high damage factor.

To solve this problem, the disinfecting washing process has to be carried out under particularly mild conditions.

However, the addition of sufficiently effective amounts of peracid compounds, even when combined with conventional light-duty detergents, leads to the above-described disadvantages in the disinfecting washing process, even at low washing temperatures, such as 30° C. to 40° C.

For this reason, other active ingredients for the disinfecting washing of textiles have been investigated in the prior art.

It has been found that disinfectants based on quaternary ammonium compounds do not generally have an adequate disinfecting effect in the disinfecting washing process at low temperatures. Serious damage to textiles was observed in tests using aldehyde-based disinfectants.

By using the surface-active compositions to be used in accordance with the invention, the disinfecting washing process can be carried out particularly gently because the textiles suffer very little damage by virtue of the elimination of the oxidizing disinfectants normally used, such as peracetic acid for example.

In another preferred embodiment, animal hooves, skin, tableware, textiles, tiles, wall, floor coverings, wood and stone surfaces and floors and walls, work surfaces, exterior surfaces of machines, minor components of machines, medical instruments and/or equipment, coated and/or uncoated tanks and/or other containers, pipes, conveyor belts and drums can be cleaned and/or disinfected with the surface-active compositions to be used in accordance with the invention.

A preferred special application of the surface-active compositions to be used in accordance with the invention is in the aseptic or substantially sterile packaging of microbiologically sensitive foods, especially ice tea, apple "schorle", alcoholic and/or alcohol-free beer, milk, yoghurt. In a particularly preferred embodiment, the food packs are treated with formulations to be used in accordance with the invention before being filled with the microbiologically sensitive products and/or surfaces located in the vicinity of the sterile packaging process, including food-carrying pipes, tanks, equipment, machines, conveyors and conveyor installations, rinsers, container manufacturing units, are treated with formulations to be used in accordance with the invention.

Accordingly, the surface-active compositions to be used in accordance with the invention are preferably used in the home, in the food manufacturing and processing industry, for example in the beverage, dairy and fish industry and in abattoirs, in gastronomy and catering, in beverage production, in milk production and processing, in the cosmetics and pharmaceutical industry, in hospitals, laundries, large kitchens, in the cleaning of buildings, for example by professional cleaners, and in agriculture.

In the production of the surface-active compositions to be used in accordance with the invention, at least one of the nonionic surfactants corresponding to formula (I) or (II) is preferably heated to temperatures in the range from 60 to 120° C., the additional constituents are dissolved or dispersed in the nonionic surfactant at those temperatures and the resulting mixture is cooled to temperatures in the range from 40° C. to room temperature, optionally after addition of the second nonionic surfactant.

In cases where constituents solid at room temperature are to be added in this preferred production process, they are preferably mixed with the nonionic surfactant corresponding to formula (I) or (II) at temperatures in the range from 70 to 90° C.

If both nonionic surfactant corresponding to formula (I) and nonionic surfactant corresponding to formula (II) are to be used in this preferred production process, the nonionic surfactant (I) or (II) which is to be used in the smaller quantity is preferably introduced first and heated, the foam regulator, if any, is added and a polycarboxylic acid or an alkali metal salt thereof, as mentioned in detail in the description of the sequestering agents, and then optionally a synthetic anionic surfactant and lastly the nonionic surfactant (I) or (II) which was not introduced before are incorporated in the mixture.

The present invention also relates to paste-form, substantially water-free thixotropic disinfectant preparations which contain a composition to be used in accordance with the invention and which, without the application of shear forces, have such a viscosity that they do not flow under the effect of gravity at room temperature, but have a distinctly lower viscosity and flow under the effect of gravity when subjected to shearing.

In a preferred embodiment, preparations such as these have a viscosity of more than 50,000 mPa.s and more particularly in the range from 100,000 to 500,000 mPa.s, as measured at 25° C. with a Brookfield® DV-II or DV-II Plus rotational viscosimeter (spindle No. 7), at 5 r.p.m. and a viscosity of less than 100,000 mPa.s and more particularly in the range from 8,000 mPa.s to 90,000 mPa.s at 50 r.p.m.

In a preferred embodiment, this paste-form, substantially water-free thixotropic disinfectant preparation contains 20% by weight to 80% by weight of the surface-active composition to be used in accordance with the invention and 20% by weight to 80% by weight of solid powder-form constituents with a mean particle size of 2 μm to 100 μm, preferably 10 μm to 80 μm and more particularly 20 μm to 60 μm and has a viscosity at 20° C. of 10,000 to 500,000 mPa.s at a shear rate of 0.025 s$^{-1}$, a viscosity at 20° C. of 5,000 to 130,000 mPa.s and more particularly in the range from 5,000 mPa.s to 13,000 mPa.s at a shear rate of 0.2 s$^{-1}$ and a viscosity at 20° C. of 400 mPa.s to 10,000 mPa.s and more particularly in the range from 400 mPa.s to 1,600 mPa.s at a shear rate of 2 s$^{-1}$.

The shear rates mentioned in the specification are measured using a Carrimed® CS 100 plate viscosimeter with a 2 cm cross-hatch flat plate (gap between plates 1.5 cm).

The present invention also relates to the production of a paste-form, substantially water-free, thixotropic disinfectant preparation in which the other solid constituents—which may be present individually or as mixtures containing two or more powder components—are added to the surface-active composition to be used in accordance with the invention introduced beforehand at temperatures of room temperature to 40° C. in a standard stirred tank reactor, care being taken to avoid any excessive introduction of air.

In a preferred embodiment, the component which, among the solid constituents, makes up the largest quantitative part of the solid phase is added last. This procedure is most particularly preferred where this component is an alkali metal silicate. The fine-particle main component may also be added at intervals, i.e. portions of the main component, more particularly alkali metal silicate, may be added in alternation with the solid secondary components. After the solids have been mixed with the surfactant premix, the paste formed is preferably ground in a mill, for example a colloid mill, to the particle size indicated for the solid phase unless the fine-particle solids used already have the required particle sizes. The ground solid constituents are then preferably subjected to final mixing with the liquid phase in another stirred tank reactor. In this final mixing step, heat-sensitive minor components in particular, for example bleaching agents, dyes and/or perfumes and enzymes, more particularly proteases, amylases, lipases and/or cellulase and optionally enzyme stabilizers, more particularly lower carboxylic acids or calcium compounds, may be incorporated in the paste.

EXAMPLES

Example 1

In a series of tests, the antimicrobial action spectrum of various nonionic surfactants (NIO surfactants) corresponding to formula (III):

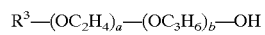

$$R^3\text{—}(OC_2H_4)_a\text{—}(OC_3H_6)_b\text{—}OH \quad\quad (III)$$

was investigated by the DGHM suspension test. All the surfactants used in these tests were investigated in the form of alkaline aqueous solutions with a surfactant concentration of 0.11%. The surfactant-containing alkaline aqueous solutions were prepared from surfactant concentrates containing 5 to 100% by weight of the corresponding surfactant. The pH value of the test solutions was adjusted to 11.3 by addition of NaOH.

The suspension test was carried out to the DGHM guidelines (J. Borneff et al. Richtlinien für die Prüfung und Bewertung chemischer Desinfektionsverfahren, Zbl. Bakt. I. Abt., B 172 (1981) 504–562). A bacterial suspension was introduced into the particular surfactant concentration to be tested at the test temperature. After specific contact times, an aliquot of the mixture was removed and the effect of the disinfecting surfactant was stopped immediately by dilution and neutralization (inactivation) with suitable substances. The number of surviving test germs was then determined by counting the number of colonies using the so-called surface technique. For comparison, a corresponding test was carried out with water instead of disinfectant at 20° C. The difference between the common logarithms of the colony numbers with and without the effect of the disinfectant gives the logarithmic reduction factor (RF).

The results are set out in Table 1. The Table refers to formula (III) where a is the average degree of ethoxylation, b is the average degree of propoxylation and c is the sum of a and b. $R^3$ corresponds to the alkyl moiety of the nonionic surfactant which is unbranched and saturated unless otherwise indicated in the Table.

*Enterococcus faecium* (ATCC 6057) was used as the test germ for determining antimicrobial activity. To simulate an organic challenge, 0.2% BSA (bovine serum albumin) was used in the suspension test. The destruction results were determined on the one hand after 1 minute and on the other hand after 5 minutes.

TABLE 1

Antimicrobial activity of selected NIO surfactants with saturated alkyl groups $R^3$ varying in length and degrees of ethoxylation (a) and propoxylation (b) at 60° C. as determined by the DGHM suspension test.

| Chemistry of the NIO surfactant corresponding to formula (III) | | | | RF v. *Enterococcus faec.* | |
| --- | --- | --- | --- | --- | --- |
| Surfactant No. | $R^3$ | a | b | c | After 1 min. | After 5 min. |
| 1 | $C_{11}$ | 1 | 0 | 1 | 3.11 | >4.97 |
| 2 | $C_{11}$ | 0 | 1 | 1 | <1.10 | >4.97 |
| 3 | $C_{12/14}$ | 3 | 0 | 3 | 2.06 | >4.76 |
| 4 | $C_{13/15}$ | 4 | 0 | 4 | 1.70 | 4.04 |
| 5 | i-$C_{13}$ | 5 | 0 | 5 | 1.36 | >4.76 |
| 6 | $C_{12/14}$ | 5 | 4 | 9 | <0.93 | 2.78 |
| 7 | $C_{12/14}$ | 7 | 0 | 7 | <1.35 | 3.03 |
| 8 | $C_{13/15}$ | 7 | 0 | 7 | 1.04 | 3.80 |
| 9 | $C_{16/18}$ | 5 | 0 | 5 | <1.35 | 1.45 |
| 10 | $C_{12-18}$ | 10 | 0 | 10 | <0.93 | 1.39 |
| 11 | $C_{16/18}$ | 14 | 0 | 14 | <1.35 | <0.99 |

RF values = germ reduction in LOG stages

It can be seen from the results in the Table that the antimicrobial performance of surfactant-containing solutions can be considerably improved by selected NIO surfactants. It can also be seen that NIO surfactants above all with certain alkyl chain lengths and certain degrees of ethoxylation or propoxylation support the disinfecting performance of surfactant-containing solutions. This is particularly important because, as a result, the choice of nonionic surfactants against the background of use in cleaning and disinfecting processes with greater emphasis on the hygiene aspect assumes a much higher place value than was the case in the past.

Example 2

In this Example, two paste-form products containing surface-active compositions according to the invention were tested for their microbicidal activity against *Enterococcum faecium* in a chemothermal laundry disinfection test.

Particulars of the test procedure can be found inter alia in the report of the Desinfektionsmittelkommission der Deutschen Gesellschaft für Hygiene und Mikrobiologie in the journal Hyg. Med., Vol. 23 1998, No. 4, page 127.

The formulations of the test pastes are shown in Table 2.

TABLE 2

Composition of paste-form disinfecting detergent formulations

| | % by weight in the formulation | |
| --- | --- | --- |
| Raw materials | Paste 1 | Paste 2 |
| NIO surfactant (III), $R^3 = C_{12/14}$ and a = 3, b = 0, c = 3 | 26 | 10 |
| NIO surfactant (III), $R^3$ = i-$C_{13}$ and a = 3, b = 0, c = 3 | 12 | 23 |
| Isotridecanol | 0 | 5 |
| Alkyl benzenesulfonate | 2.5 | 2.5 |
| Nitrilotriacetic acid (NTA) | 4 | 4 |
| Polyacrylate | 6 | 6 |
| Sodium phosphonate | 1 | 1 |
| Sodium metasilicate | 46 | 46 |
| Optical brightener | 0.5 | 0.5 |
| Foam inhibitor | 1 | 1 |
| $C_{16/22}$ Fatty acid sodium salt | 1 | 1 |

The test conditions of the microbiological tests carried out with these formulations were as follows:

Test Conditions:

| | |
| --- | --- |
| Test 1: | 3 g paste 1 per liter wash liquor |
| Test 2: | 3 g paste 2 per liter wash liquor |
| Wash liquor: | 37.5 liters |
| Laundry: | 7.5 kg prewashed disinfected kitchen towels (dry laundry) |
| Solvent: | softened water, 0° dH |
| Contact time and test temperatures: | 5 minutes 30° C. (actual temp.: 30° C. (tests 1 and 2)) + 15 mins. 60° C. (actual temp.: 60° C. (tests 1 and 2)) |
| Challenge: | 12.5 ml defibrinated sheep's blood per kg dry laundry |
| Germ spectrum: | *Enterococcus faecium* ATCC 6057 (K 3330) |
| Deactivator: | TLH-Na thiosulfate |
| Test duration: | 4 weeks |

Results:

The results are set out in detail in Tables 3 and 4.

Under the test parameters applied, the test standards for an effective laundry disinfection process, according to which 1. the number of test germs on the germ carriers must be reduced by 6 log stages by the process and at the same time
2. no test germs should be detectable on the previously sterile germ carriers washed in the test, were fulfilled by both products after a contact time of 15 minutes at 60° C. in a Frista washing machine

TABLE 3

Chemothermal laundry disinfection in test 1
Results expressed as reduction factors (RF) after a contact time of 15 minutes at 60° C.
Paste 1 (3 g/l wash liquor)

| Test germ | Germ count per germ carrier | Control values for determining the RF values | Individual values (RF) | Test germ content on 3 sterile, washed germ carriers |
|---|---|---|---|---|
| Enterococcus faecium ATCC 6057 | $5.86 \times 10^7$ | 7.77 | 7.55 | <1 |
| | | | 7.25 | <1 |
| | | | >7.77 | <1 |
| | | | 7.25 | <1 |
| | | | 7.25 | <1 |

TABLE 4

Chemothermal laundry disinfection in test 2
Results expressed as reduction factors (RF) after a contact time of 15 minutes at 60° C.
Paste 2 (3 g/l wash liquor)

| Test germ | Germ count per germ carrier | Control values for determining the RF values | Individual values (RF) | Test germ content on 3 sterile, washed germ carriers |
|---|---|---|---|---|
| Enterococcus faecium ATCC 6057 | $3.71 \times 10^7$ | 7.57 | >7.57 | <1 |
| | | | >7.57 | <1 |
| | | | >7.57 | <1 |
| | | | >7.57 | <1 |
| | | | >7.57 | <1 |

We claim:

1. A method for disinfecting a surface comprising contacting the surface with a concentrated composition comprising:

a) 5 to 100% by weight of one or more nonionic surfactants corresponding to general formula (I):

$$R^1-(OC_2H_4)_n-(OC_3H_6)_m-OH \quad (I)$$

in which $R^1$ is a linear or branched alkyl or alkenyl group containing 10, 12 or 14 carbon atoms and the sum of the average degree of ethoxylation n and the average degree of propoxylation m is between 0.5 and 5, and b) 5 to 100% by weight of one or more nonionic surfactants corresponding to general formula (II):

$$R^2-(OC_2H_4)_r-(OC_3H_6)_s-OH \quad (II)$$

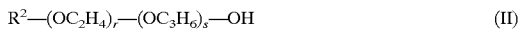

in which $R^2$ is a linear or branched alkyl or alkenyl group containing 9, 11 or 13 carbon atoms and the sum of the average degree of ethoxylation r and the average degree of propoxylation s is between 0.5 and 5, wherein the ratio by weight of nonionic surfactant corresponding to general formula (I) to nonionic surfactant corresponding to general formula (II) is between 4:1 and 1:4, the sum total of all constituents not exceeding 100% by weight, to provide disinfection.

2. The method claimed in claim 1, wherein the composition comprises 0.5 to 35% by weight of anionic surfactant solid at room temperature.

3. The method claimed in claim 1, wherein the composition contains 5 to 60% by weight of nonionic surfactant corresponding to general formula (I) and/or 5 to 60% by weight of nonionic surfactant corresponding to general formula (II).

4. The method claimed in claim 1, wherein the composition contains 5 to 40% by weight of nonionic surfactant corresponding to general formula (I) and/or 5 to 40% by weight of nonionic surfactant corresponding to general formula (II).

5. The method claimed in claim 1, wherein, for the nonionic surfactant corresponding to formula (I), the sum of the average degree of ethoxylation n and the average degree of propoxylation m is between 1 and 3 and, for the nonionic surfactant corresponding to formula (II), the sum of the average degree of ethoxylation r and the average degree of propoxylation s is between 1 and 3.

6. The method claimed in claim 1, wherein the composition contains additional components with complexing properties and/or solubilizers and/or surface-active components.

7. The method claimed in claim 1, wherein additional antimicrobial components selected from alcohols, aldehydes, antimicrobial acids, carboxylic acid esters, acid amides, phenols, phenol derivatives, diphenyls, diphenylalkanes, urea derivatives, oxygen and nitrogen acetals and formals, benzamidines, isothiazolines, phthalimide derivatives, pyridine derivatives, antimicrobial surfactants, guanidines, antimicrobial amphoteric compounds, quinolines, 1,2-dibromo-2,4-dicyanobutane, iodo-2-propynyl butyl carbamate, iodine, iodophores, peroxides are present.

8. The method claimed in claim 1, wherein the composition is formulated as at least one of an aqueous solution, gel, emulsion, paste, dispersion, solid shaped body or powder.

9. The method claimed in claim 1, wherein the step of contacting the composition with a surface to be disinfected comprises immersing the surface in the composition.

10. The method claimed in claim 1, wherein the step of contacting comprises washing and disinfecting textiles with the composition at a temperature in the range from 10 to 70° C.

11. The method claimed in claim 10, wherein disinfection is achieved without the addition of per acids.

12. The method claimed in claim 1, wherein the composition comprises a paste-form, substantially water-free thixotropic disinfectant preparation which, without the application of shear forces, has such a viscosity that it does not flow under the effect of gravity at room temperature, but has a distinctly lower viscosity and flows under the effect of gravity when subjected to shearing.

13. The method claimed in claim 12, wherein the composition has a of more than 100,000 mPa.s as measured with a Brookfield® DV-II or DV-II Plus rotational viscosimeter (spindle No. 7), at 5 r.p.m. and a viscosity of less than 100,000 mPa.s at 50 r.p.m.

14. The method claim in claim 1, wherein the composition comprises a paste-form, substantially water-free thixotropic disinfectant preparation containing 20% by weight to 80% by weight of the composition to be used and 20% by weight to 80% by weight of solid powder-form constituents with a mean particle size of 5 μm to 100 μm, the composition having a viscosity at 20° C. of 10,000 to 500,000 mPa.s at a shear rate of 0.025 s$^{-1}$, a viscosity at 20° C. of 5,000 to 130,000 mPa.s at a shear rate of 0.2 s$^{-1}$ and a viscosity at 20° C. of 400 mPa.s to 10,000 mPa.s at a shear rate of 2 s$^{-1}$.

15. The method claimed in claim 1, wherein the composition comprises water and/or other auxiliaries and/or active substances.

16. The method claimed in claim 2, wherein the anionic surfactant comprises at least one of alkyl benzenesulfonic acid, alkali metal alkyl benzenesulfonate, and alkali metal alkyl or alkenyl sulfate.

17. The method claimed in claim 12, wherein the composition has a viscosity of 150,000 to 500,000 mPa.s as measured with a Brookfield® DV-II or DV-II Plus rotational viscosimeter (spindle No. 7), at 5 r.p.m. and a viscosity of 10,000 mPa.s to 90,000 mPa.s at 50 r.p.m.

18. The method claimed in claim 14, wherein the solid powder-form constituents have a mean particle size of 10 μm to 80 μm, the composition having a viscosity at 20° C. of 5,000 mPa.s to 13,000 mPa.s at a shear rate of $2\ s^{-1}$ and a viscosity of 400 mPa.s to 1,600 mPa.s at a shear rate of $2\ s^{-1}$.

19. The method claimed in claim 14, wherein the solid powder-form constituents have a mean particle size of 10 μm to 60 μm.

20. The method claimed in claim 1, wherein the step of contacting comprises destroying *Enterococcum faecium*.

* * * * *